United States Patent [19]

Liu

[11] Patent Number: 5,897,881

[45] Date of Patent: *Apr. 27, 1999

[54] HARD TISSUE INTACTLY DISSOLVED MATERIALS AND METHOD FOR PRODUCING THE SAME

[75] Inventor: Anjun Liu, Sapporo, Japan

[73] Assignee: Kabushiki Kaisha Sangi, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/716,226

[22] PCT Filed: Feb. 2, 1996

[86] PCT No.: PCT/JP96/00219

§ 371 Date: Sep. 23, 1996

§ 102(e) Date: Sep. 23, 1996

[87] PCT Pub. No.: WO96/23805

PCT Pub. Date: Aug. 8, 1996

[30] Foreign Application Priority Data

Feb. 2, 1995 [JP] Japan ................. 7-039134

[51] Int. Cl.⁶ .................................................. A61K 35/32
[52] U.S. Cl. ............................................... 424/549
[58] Field of Search ................................... 424/549

[56] References Cited

U.S. PATENT DOCUMENTS 4,172,128 10/1979 Thiele et al. ............................ 424/549

FOREIGN PATENT DOCUMENTS

| 59-175435 | 10/1984 | Japan | ............. A61K 35/32 |
| 59-216554 | 12/1984 | Japan | ............. A23L 1/20 |
| 61-104744 | 5/1986 | Japan . | |
| 4-16165 | 1/1992 | Japan | ............. A23L 1/305 |
| 9217167 | 10/1992 | WIPO | ............. A61K 9/50 |

OTHER PUBLICATIONS

Database–WPI, Week 9503. Abstract of RU–A–2 010 830, Apr. 15, 1994, Derwent Publications Ltd.

Database–WPI, Week 9502, Abstract of JP–A06 298 621, Oct. 25, 1994, Derwent Publications Ltd.

*Primary Examiner*—Jean C. Witz
*Attorney, Agent, or Firm*—Ladas & Parry

[57] ABSTRACT

A hard tissue intactly dissolved material including original components of hard tissues in pure (non-denatured) form and a method for producing the material are disclosed. Ground hard tissues are mixed with an edible acid and dissolved under reduced pressure. The hard tissue are mainly of mammal bones, however, mammal bone marrow, mammal teeth, shells, crustacean integument, corals, etc., may be used. Also, lactic acid may be used as the edible acid.

6 Claims, 7 Drawing Sheets

WESTERN BLOTTING

1: MARKER
2: BOVINE BONE DERIVED GUANIDINE EXTRACTED BONE FORMING PROTEINS INCLUDED FRACTION
3: MARKER
4: BONE TISSUE INTACTLY DISSOLVED MATERIAL

IMPLANTING EXPERIMENT 1   2   3

1: CONTROL
2: BOVINE BONE DERIVED GUANIDINE EXTRACTED
   BONE FORMING PROTEINS INCLUDED FRACTION
3: BONE TISSUE INTACTLY DISSOLVED MATERIAL

ALKALIPHOSPHATASE ACTIVITY

1: CONTROL
2: BOVINE BONE DERIVED GUANIDINE EXTRACTED BONE FORMING PROTEINS INCLUDED FRACTION
3: BONE TISSUE INTACTLY DISSOLVED MATERIAL

1: BOVINE BONE DERIVED GUANIDINE EXTRACTED BONE SIALOPROTEIN II
2: BONE TISSUE INTACTLY DISSOLVED MATERIAL
3: BONE TISSUE INTACTLY DISSOLVED MATERIAL
4: MARKER

HARD TISSUE INTACTLY DISSOLVED MATERIALS AND METHOD FOR PRODUCING THE SAME

FIELD OF THE INVENTION

The present invention relates to hard tissue intactly dissolved materials and method for producing the materials, and more particularly, to functional food materials ingestible to the human body, or novel materials applicable to feed, medical products, cosmetics, etc., and a method for producing such materials.

The term "hard tissue" used in this patent application is used as a general term for tissues of organisms including calcium, proteins, polysaccharides and other trace elements such as bone and bone marrow of mammals, birds and fishes, shells, crustacean integument, egg shells and corals.

BACKGROUND OF THE INVENTION

Various kinds of functional foods containing mainly calcium, which may be used as supplemental foods for osteoporosis or other bone-related diseases, are on the market. Currently, these calcium containing foods are mainly made from calcium carbonate, calcium lactate, calcium phosphate, or cattle bone powder, egg shells or fish bone powder (natural bone-derived calcium).

Although the relationship between the characteristics of calcium components ingested to the body and its degradation and intake inside the body is not completely solved, it is considered in general that intake of natural bone-derived calcium is distinctly superior to simple intake of calcium salts in terms of quick recovery from bone diseases. However, there is a disadvantage in the commercially available natural calcium based foods such as cattle bone powder or fish bone powder in their problematic ingestibility. That is, they are not fully degraded by gastric acid due to their coarse particles since they are made into powder by grinding.

A method was proposed in which mammal bones are decalcified using acidic solution in order to achieve efficient intake of calcium components (Japanese Laid-Open Patent Application No. 4-16165). This method basically provides calcium intake supplements or calcium replenishments in which soluble calcium is added to an acid soluble fraction obtained by decalcifying ground bone powder using an aqueous solution of inorganic acid such as hydrochloric acid, sulfuric acid and nitric acid or that of organic acid such as formic acid and acetic acid, or to a water soluble fraction obtained by adding an enzyme to the above fraction and hydrolyzing it, or to a fraction obtained by dialyzing the above fractions to remove bone-derived calcium salts.

More specifically, ground bone is suspended in an aqueous solution of pH 2–3 containing the above-mentioned inorganic acid or organic acid and the bone is decalcified by stirring for 30 min. to a few hours. Then protease (e.g. pepsin) is added to carry out enzymatic degradation and a resulting acid soluble fraction or water soluble fraction of molecular weight 3000 to 60000 Da is used as the calcium intake supplements, or the above fractions are further desalinized to produce fractions comprising a mixture of peptides and proteins and soluble calcium lactate or calcium carbonate is added thereto to produce the calcium replenishments.

On the other hand, mammal bones contain not only calcium but also physiologically active substances such as collagen proteins including peptides or polypeptides, amino acids, proteoglycan and trace amounts of bioactive elements. It is known that these substances other than calcium are also desirable supplements for bone related diseases from the point of view of enhancing physiological activity (hormone balance or activity of enterobacteria) which is very important in biological systems. Especially, it has been found that proteins such as BMP or BSP-II discovered recently are deeply involved with the formation of bone. Their use as pharmaceuticals has been studied.

In the meantime, since the above mentioned conventional method used strong acids to decalcify bone components, the physiological activity of components contained in products are lowered. Also, since physiologically active substances such as proteins and proteoglycan are denatured by heat generated during a grinding process of mammal bones, which is carried out before the decalcification process, the products do not contain natural components of the bone.

SUMMARY OF THE INVENTION

Therefore, the object of the present invention is to provide hard tissue intactly dissolved materials having an excellent effect on bone-related diseases and a method for producing the materials in which hard tissues are completely dissolved in a short amount of time without denaturing the original components.

To achieve the object, according to the present invention, ground hard tissues and edible acids are mixed and dissolved under reduced pressure. The hard tissues are mainly bones of mammals, birds and fishes, however, bone marrow or teeth or shells, crustacean integument and corals may also be utilized. Moreover, it is preferable to use lactic acid as the edible acid.

The completely dissolved hard tissues according to the present invention may be obtained by mixing (immersing, dissolving, suspending) bone tissues with acidic solution and dissolving them under reduced pressure. When this mixed solution is stirred in a state of reduced pressure, e.g., under vacuum, air present in fine pores of bone powder is degassed and the acidic solution goes into the pores.

When the bone powder is mixed and immersed in the edible acid under standard atmospheric pressure, a rapid and sufficient dissolution cannot be achieved since the solution cannot contact the bone due to generation of a bubbling phenomenon. However, anti-bubbling effect is increased under reduced pressure and the contact between the bone and the solution is enhanced so that the time required for the dissolving process is shortened and the dissolving efficiency is increased.

That is, in a state of removing bubbles formed, the outer surface and inner fine pores of the bone powder are completely contacted with the acidic solution and dissolved. The absolute magnitude of the acidic solution which contacts the inside of the bone tissue under reduced pressure is of tens-fold to hundreds-fold of the contact amount of the acidic solution stirred under standard atmospheric pressure. For this reason, time required for the dissolving process is remarkably shortened and, more importantly, it becomes possible to dissolve bone components intactly (the relationship between the degree of reduced pressure and the solubility is shown in FIG. 7). This is because the acidic solution makes contact with the fine bone powder from the inside and calcium, proteins, trace amount physiological active substances, etc., contained in the bone tissues are sufficiently extracted.

Since time required for the dissolving process can be reduced, denaturing of bone components due to the acidic solution is minimized as much as possible and their yield is remarkably increased.

The application of the hard tissue intactly dissolved materials according to the present invention is not limited to functional foods (especially, calcium replenishment). The materials are also applicable to pharmaceuticals, cosmetics, bone fillers (medical materials), toothpaste materials, internal pellets having sustained release property and so on.

Note that when the materials are eaten by a human as functional foods, it is necessary that they are not poisonous to the human body. From this point of view, strong acids such as hydrochloric acid cannot be used in the present invention. According to experiments conducted, use of organic acids such as acetic acid (including the one from rice), wine vinegar and formic acid is found to be preferable as the soluble solution which is not poisonous to human beings.

Also, it is confirmed that since calcium components of hard tissues have been converted to calcium lactate in the hard tissue intactly dissolved material obtained as a final product when lactic acid is used as the dissolving solution, intake of the material in a human body is very high, and the product has high physiological activity, in which all the components of the bone (tissue) are kept intact.

PREFERABLE EMBODIMENTS OF THE PRESENT INVENTION

Figure 1:
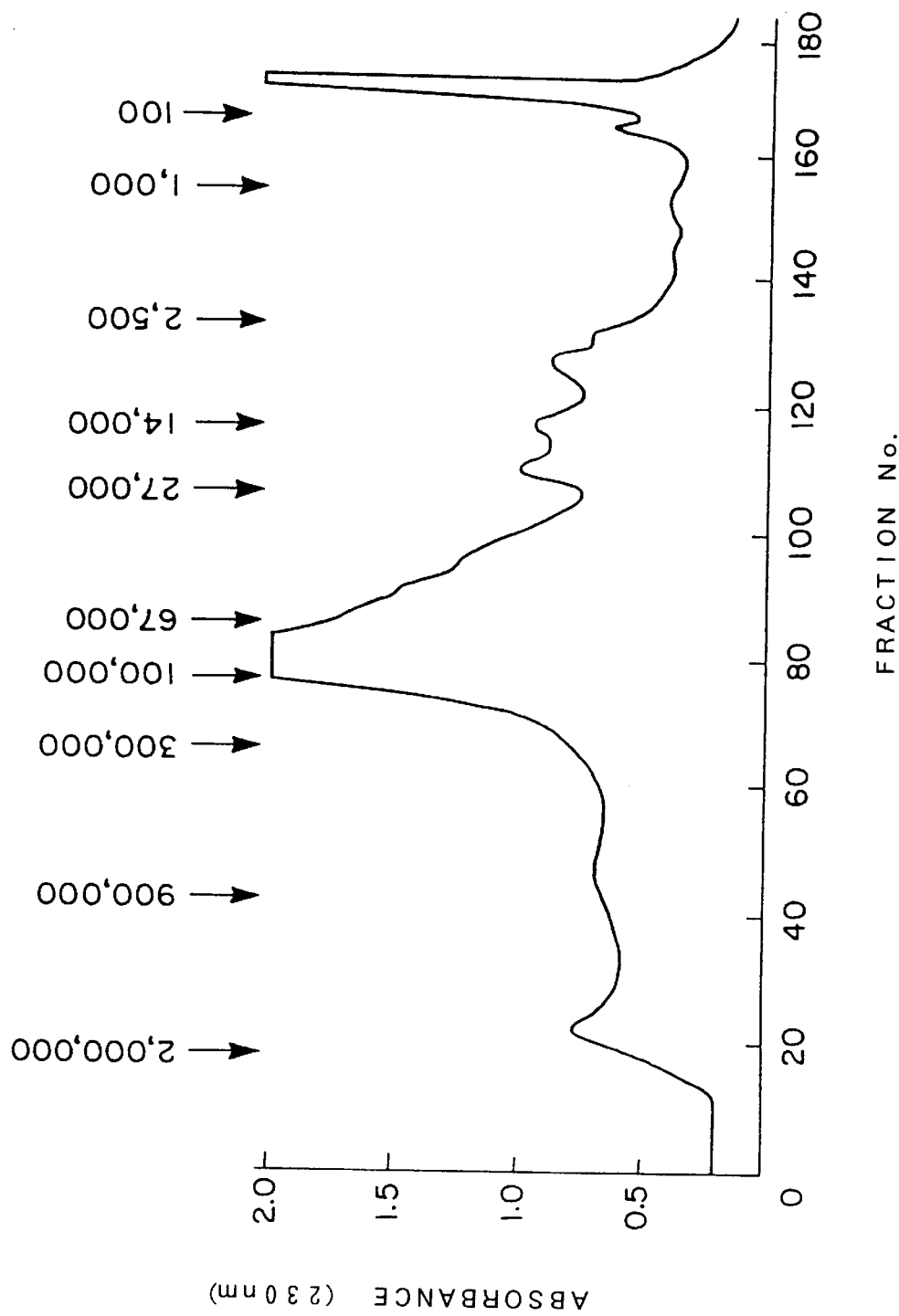
FIG.1 shows a chromatogram of an example of the hard tissue intactly dissolved materials according to the present invention.
Figure 2:
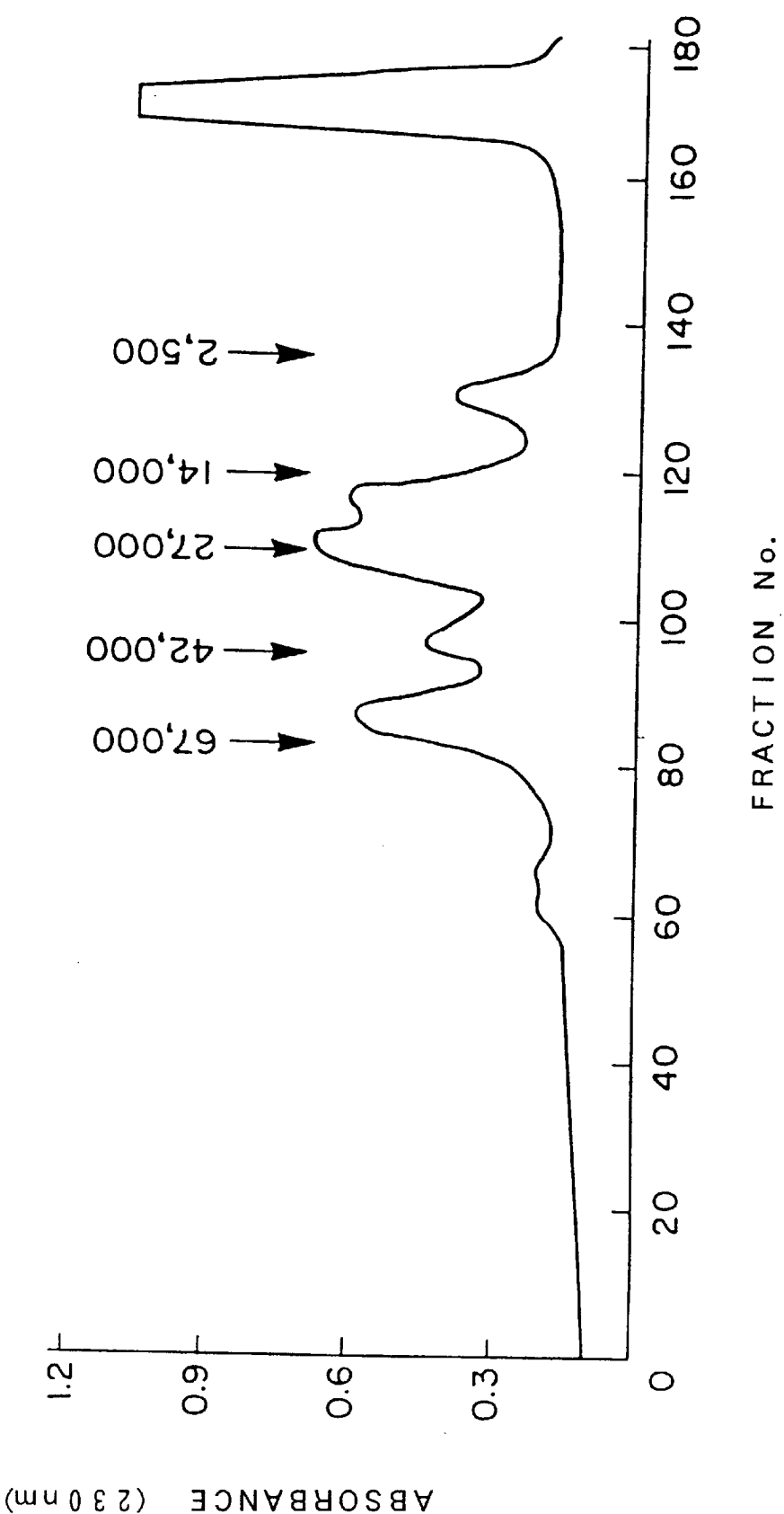
FIG.2 shows a chromatogram of decalcificated components of a mammal hard tissue obtained using a conventional method.

FIG.1 is an example of chromatograph showing components of the hard tissue intactly dissolved materials according to the present invention. As shown, the molecular weight of organic matter originally contained in the hard tissue may be confirmed to be a minimum of hundreds Da to a maximum of two million Da or more. However, using the conventional method, organic matter in a small range, from 3000 to 60000 Da, can only be obtained as shown in FIG. 2. This indicates that components having high physiological activity are lost during the decalcification and desalinization processes. On the other hand, according to the present invention, it is possible to obtain organic matter such as proteins (including peptides) and polysaccharides of molecular weight between 100 and two million Da without losing components having high physiological activities.

Embodiments

The hard tissue intactly dissolved materials according to the present invention may be obtained, for example, using the following procedure.

First, mammal bones or fish shells are ground, while generation of heat is restrained as much as possible, until their particle size becomes appropriate. The ground particles are then washed with water. It is preferable that the particle size is no more than five mm, for instance. After washing, the particles are mixed with the lactic acid solution of appropriate concentration, e.g., 10 percent, and the container containing the solution is placed in a degassing apparatus and is left under reduced pressure while the solution is stirred. In this case, as the rate of degassing is increased, the rate of dissolving process of the hard tissue is increased. Alteration of the components due to the reduced pressure could not be confirmed. Thus, in order to reduce the process time as much as possible, it is necessary to stir the solution in a state which is as close as possible to a vacuum condition. Although the temperature of stirring is not limited, it is desirable to use a low temperature (for example, from 0 degree to 20 degrees), preferably about four degrees, in order to prevent the growth of bacteria and so on.

All the components of the mammal bones and fish shells may be completely dissolved after five to six hours of stirring under the above mentioned vacuum condition. The process time may be significantly reduced compared with the case in which no reduction of pressure is carried out. Moreover, if reduction of pressure is not carried out, not all the components of the bone tissue can be dissolved. However, by reducing the pressure, all the components can be dissolved without denaturing.

The yield of calcium, organic matter and trace elements contained originally in hard tissues is significantly increased under the above-mentioned reduced pressure condition (not necessarily a vacuum condition) compared with the case in which no reduction of pressure is carried out. It was found that when 10% lactic acid solution and reduced pressure condition (e.g. vacuum condition) are employed, the above-mentioned yield is increased to about six to ten-fold compared with the yield under non-reduced pressure.

Also, it is possible to obtain calcium, organic matter and trace elements originally contained in hard tissues substantially intact. That is, although the molecular weight of proteins (including peptides) contained in normal natural hard tissues ranges from hundreds to two million Da as shown in FIG.1, the molecular weight of hard tissue dissolved materials obtained under non-reduced pressure condition is merely in the range of 3000 to 60000 Da as shown in FIG.2. On the other hand, it is possible to obtain hard tissue components whose molecular weight range from 100 to two million Da when the hard tissue particles-lactic acid mixed solution is stirred under reduced pressure.

The hard tissue intactly dissolved materials according to the present invention are materials in which proteins are dissolved in non-denatured state and the materials are considered to be including proteins having sufficient physiological activities. For this reason, existence or non-existence of BSP-II (bone sialoprotein II) and BMP (bone morphogenetic protein) in hard tissue intactly dissolved materials, and physiological activity of BMP are investigated.

Figure 3:
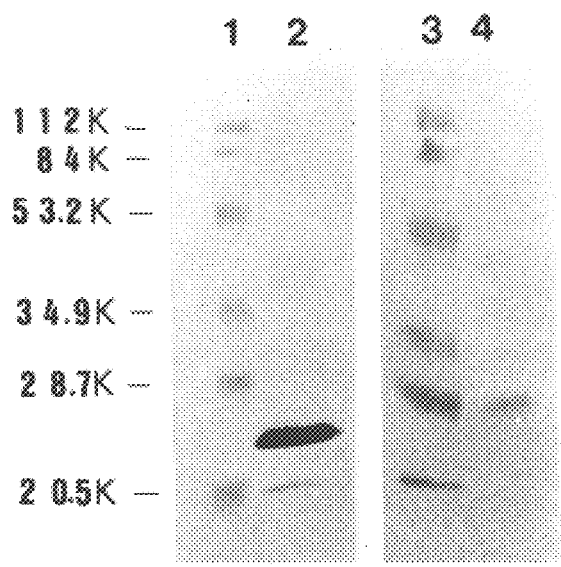
FIG.3 shows Western blotting indicating existence of BMP in a hard tissue intactly dissolved material.

FIG.3 shows a study on existing BMP in a hard tissue intactly dissolved material. The Western blotting method was used and the confirmation was made using anti-bovine BMP-2 monoclonal antibody. As a result, a band of about 24000 molecular weight which responded to the anti-bovine BMP-2 monoclonal antibody was detected in lane 2. On the other hand, the same type of band was detected at the region of about 28000 molecular weight in lane 4. This indicates that BMP existed in the hard tissue intactly dissolved materials and that it existed in a more intact state compared with the one from the guanidine extracted method which is generally carried out.

Then, in order to determine if the protein has a physiological activity, its bone forming ability was examined by implanting the materials underneath the skin along a back region of a rat.

Figure 4:
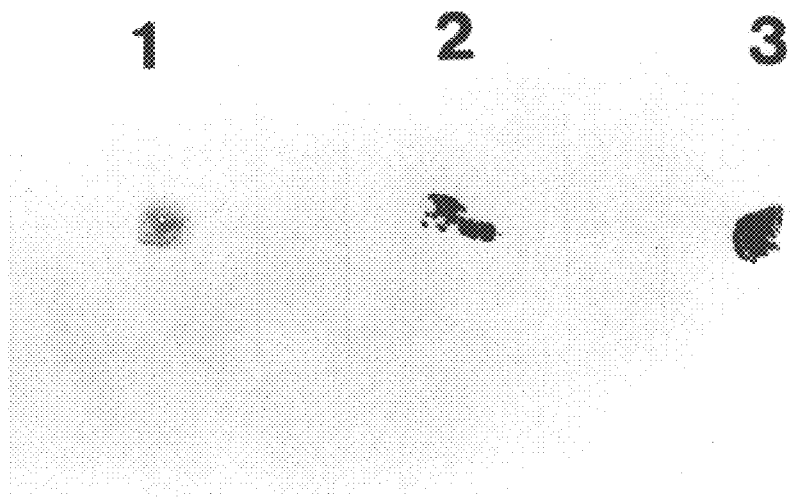
FIG.4 is a diagram constructed based on soft X-ray photograph taken after an experiment in which the hard tissue intactly dissolved materials are implanted underneath the back region skin of a rat.

FIG. 4 is a diagram constructed based on soft X-ray photograph taken after the experiment in which the hard tissue intactly dissolved materials are implanted underneath the skin along a back region of a rat. Since opaque images are shown in 2 and 3, it is evidenced that the hard tissue intactly dissolved materials has bone forming ability.

Figure 5:
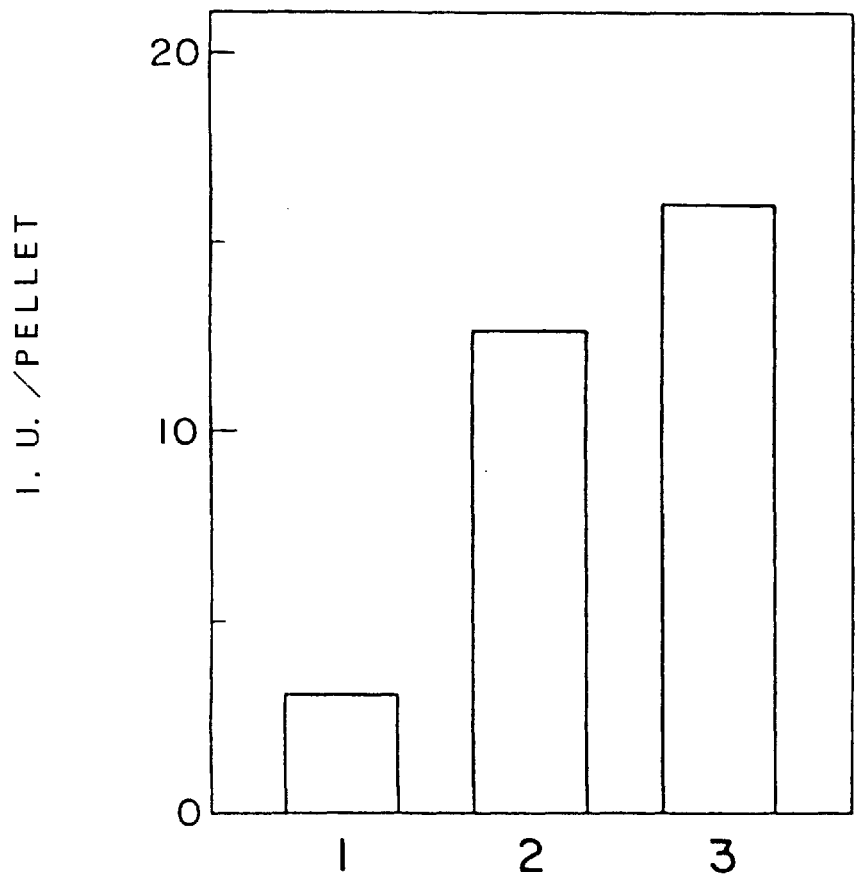
FIG.5 is a diagram showing measured values of alkaliphosphatase activity of the hard tissue intactly dissolved material.

FIG. 5 shows results of measuring values of alkaliphosphatase activities of pellets which were calcificated. The values of 2 and 3 are obviously higher than that of 1 which is a control and the activity of 3 is a little higher than that of 2. Therefore, it is considered that the opaque image shown in FIG. 4 was not due to simple deposits of calcium and showed the bone inducing activity.

Figure 6:
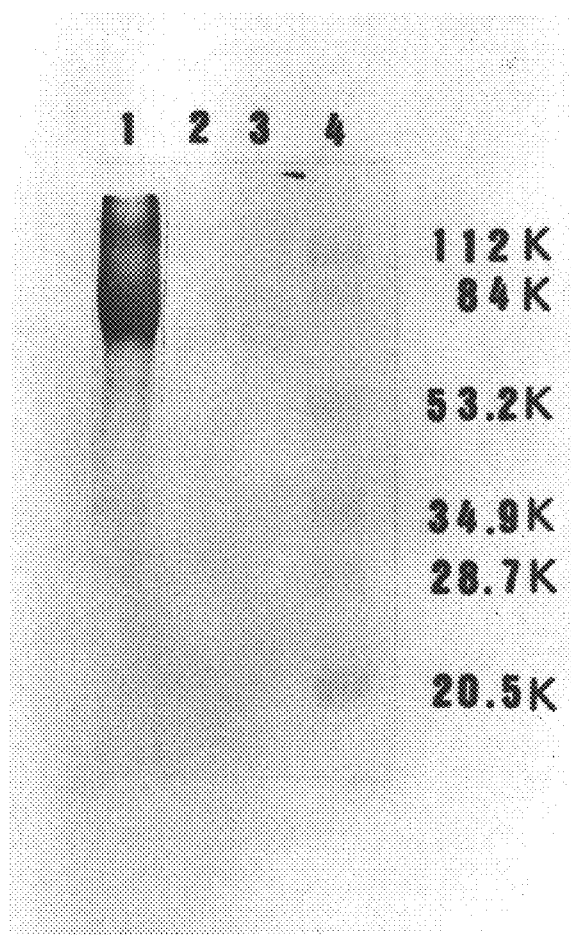
FIG.6 shows Western blotting indicating an existence of BSP-II in hard tissue intactly dissolved materials.
Figure 7:
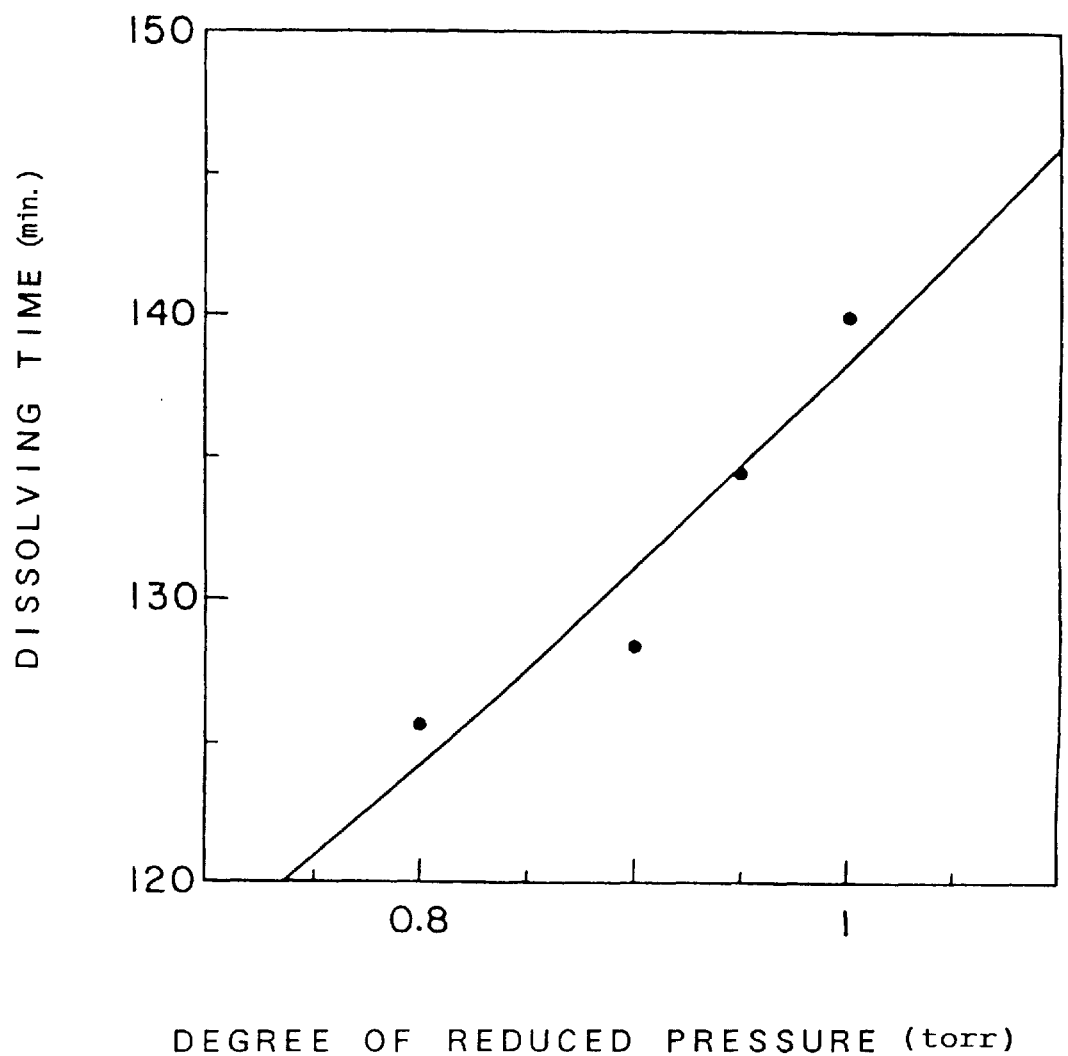
FIG.7 is a graph showing the relationship between the degree of reduced pressure and the solubility.

FIG. 6 shows the examination of an existence of BSP-II in hard tissue intactly dissolved materials. The Western blotting method using the anti-bovine BSP-II monoclonal antibody was employed. As shown in the figures, bands which responded to the anti-bovine BSP-II monoclonal antibody were detected in the hard tissue intactly dissolved materials (in lanes 2 and 3).

As mentioned above, the existence of proteins involved in bone formation such as BMP and BSP-II, whose use in treatment of bone-related diseases, e.g., osteoporosis have drawn attention recently, in the hard tissue intactly dissolved materials was confirmed. Thus the hard tissue intactly dissolved materials according to the present invention can provide not only the calcium salts supplements but also various products which contribute to recovery of bone-related diseases by supplying proteins, which enhance the formation of bone, together with other trace amount physiologically active elements.

Also, when lactic acid and reduced pressure condition are used, bone calcium may be obtained mainly in the form of soluble calcium. When the calcium is used as a functional food, its digestibility is far more excellent than the other calcium salts.

The hard tissue intactly dissolved materials according to the present invention may be produced without using the lactic acid solution. When milk (dry milk) (and sugar if necessary) is added to the hard tissue powder and lactic acid bacterium is further added to it with stirring at a temperature higher than room temperature, e.g., 37 degrees, the milk is converted to a lactic acid solution and dissolves the hard tissue powder. Thus, if the lactic acid bacterium is added to milk and mixed with the hard tissue powder under the reduced pressure condition, it is possible to intactly dissolve the natural hard tissue components in a short amount of time similar to the above-mentioned embodiment. In this case, it is preferable that the initial temperature is high, however, if the pressure is reduced when the milk is converted to the lactic acid solution, the same result as the previous embodiment may be obtained. Note that the process time becomes a little longer if the above conditions are used due to the time required for conversion to lactic acid.

Also, the hard tissue intactly dissolved materials according to the present invention are not limited to the ones obtained by the process described in the above mentioned embodiment. For example, the edible acid is not limited to lactic acid. The reason that lactic acid is used in the above embodiment is to obtain a dissolved material, which can be eaten with least resistance in terms of taste and other factors, on the assumption that the material is eaten directly as a recovering agent from bone-related diseases or a functional food. Thus, if dissolved materials which are not poisonous to human being can be obtained, it is not necessary to use the lactic acid as a dissolving solution. If the same result can be obtained, it is possible to use acetic acid, citric acid, acidic juices, etc., as the dissolving solution. Not to mention that, if the final product (the hard tissue intactly dissolved materials) is not used as a food material, it is possible to use non-edible acids such as hydrochloric acid.

Although it is explained that the mixture of the bone tissue powder and the lactic acid solution in the container is stirred under reduced pressure condition (e.g., vacuum condition) in the previous embodiment, the meaning of using the reducing pressure is to ease the contact of the acidic solution to the interspace of a powder particle. Therefore, it is preferable to increase the number of contacts between the interspace of a hard tissue powder and the acidic solution in order to enhance a dissolving effect. Thus, it is possible to change the degree of reduced pressure so that the acidic solution which goes into interspace of fine pores can move. For example, after 30 minutes of stirring under vacuum, the pressure is returned to atmospheric for five minutes and then back to vacuum for 30 minutes, and this pattern is repeated. The time of a pattern is not particularly limited. It is acceptable if the pattern repeats reduction and non-reduction of pressure by which the dissolution of hard tissue powder is completed in a short amount of time.

Possible use in industry

Since the hard tissue intactly dissolved materials according to the present invention includes not only calcium but also bone forming proteins such as BMP and BSP-II, in intact form, whose use in treatment of bone-related diseases (osteoporosis) have drawn attention recently, it is possible to provide functional foods which have positive effects on bone formation necessary for the bone-related diseases such as osteoporosis. Moreover, when a lactic acid is used as dissolved agent, since it is obtained in the form of soluble calcium, its digestibility as a functional food is far more excellent compared with other calcium salts.

I claim:

1. A method for dissolving bone material consisting essentially of mixing said bone material with an edible lactic acid solution under reduced pressure.

2. The method according to claim 1, wherein said lactic acid solution is obtained by adding lactic acid bacterium to milk and stirring at a temperature no less than room temperature.

3. The method according to claim 1 or 2, wherein said reduced pressure is returned to ordinary pressure at least once.

4. The method according to claim 1 or 2, wherein the temperature used for dissolving said mixture under reduced pressure is between 0 and 20° C.

5. The method according to claim 1, wherein the temperature used for dissolving said mixture under reduced pressure is between 0 and 20° C., and wherein said reduced pressure is returned to ordinary pressure at least once.

6. A method for producing a dissolved bone material including organic matter in a non-denatured state consisting essentially of mixing ground bone material and an acid and said mixture is dissolved under reduced pressure, wherein said acid comprises an edible lactic acid solution, wherein said lactic acid solution is obtained by adding lactic acid bacterium to milk and stirring at a temperature no less than room temperature, and wherein said reduced pressure is returned to ordinary pressure at least once.

\* \* \* \* \*